United States Patent
Villeponteau et al.

(10) Patent No.: US 9,744,204 B1
(45) Date of Patent: Aug. 29, 2017

(54) MULTIPATH NUTRITIONAL SUPPLEMENT FOR MEMORY, COGNITION, AND COORDINATION

(71) Applicants: Bryant Richard Villeponteau, San Diego, CA (US); Cristina Rizza, Corona Del Mar, CA (US)

(72) Inventors: Bryant Richard Villeponteau, San Diego, CA (US); Cristina Rizza, Corona Del Mar, CA (US)

(*) Notice: Subject to any disclaimer, the term of this patent is extended or adjusted under 35 U.S.C. 154(b) by 0 days.

(21) Appl. No.: 15/073,321

(22) Filed: Mar. 17, 2016

Related U.S. Application Data

(60) Provisional application No. 62/133,998, filed on Mar. 17, 2015.

(51) Int. Cl.
| | | |
|---|---|---|
| *A01N 65/00* | (2009.01) |
| *A61K 36/8988* | (2006.01) |
| *A61K 36/45* | (2006.01) |
| *A61K 31/197* | (2006.01) |
| *A61K 36/481* | (2006.01) |

(52) U.S. Cl.
CPC ........ *A61K 36/8988* (2013.01); *A61K 31/197* (2013.01); *A61K 36/45* (2013.01); *A61K 36/481* (2013.01)

(58) Field of Classification Search
CPC ...................................................... A61K 36/00
USPC ........................................................... 424/725
See application file for complete search history.

(56) References Cited

FOREIGN PATENT DOCUMENTS

CN 103689235 A * 4/2014

\* cited by examiner

*Primary Examiner* — Michael Meller
(74) *Attorney, Agent, or Firm* — Oppedahl Patent Law Firm LLC

(57) ABSTRACT

Synergistic compositions of 4, 8, 12, and 13 medicinal components and various combinations thereof that provide multipath synergistic nutritional support for memory, cognition, and neuromuscular coordination in humans, cats, dogs, and horses and provide preventive treatments for various neurological diseases. The composition including a mixture of *Astragalus membranaceus* (Huang Qi) roots, *gastrodia elata* tuber, *Vaccinium uliginosum* berries, L-Theanine, Genistein, Berberine, *Schisandra chinensis* berry extract, lithium, selenium, piperine, Methyl Folate, and Astragaloside IV.

19 Claims, 6 Drawing Sheets

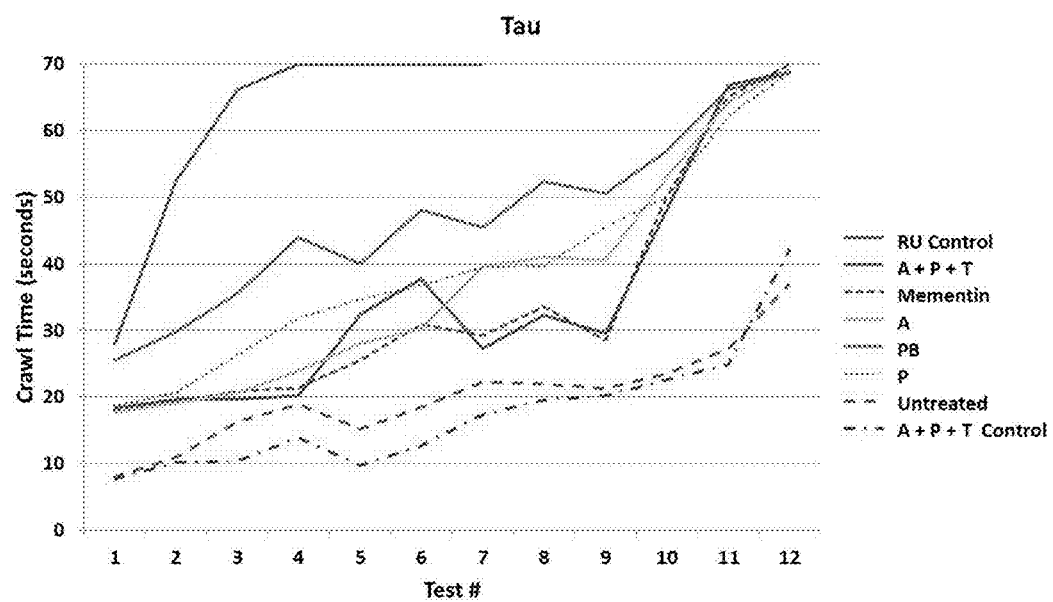
Fig. 1A: Crawl Test with Tau gene for selected substances.

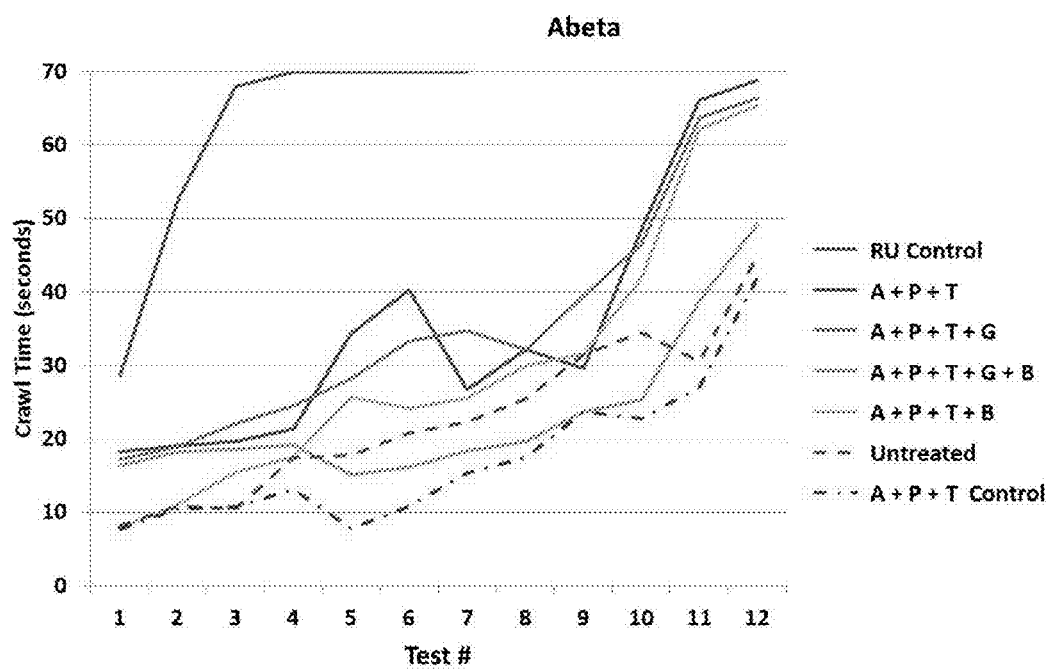
Fig. 1B: Crawl Test with Abeta gene for selected combinations.

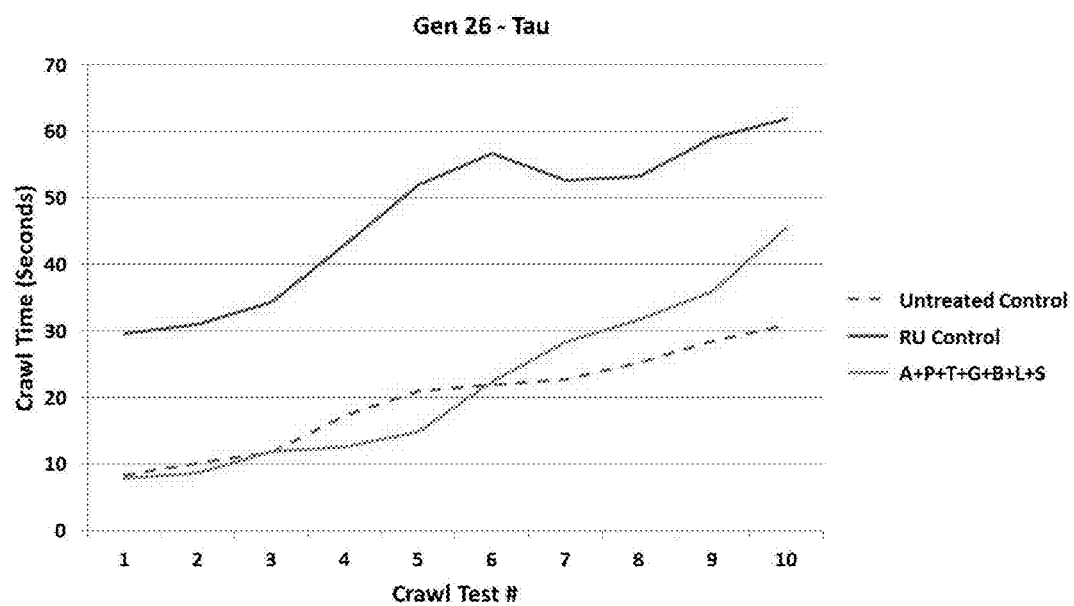
Fig. 2: Crawl Test with tau gene for best combination.

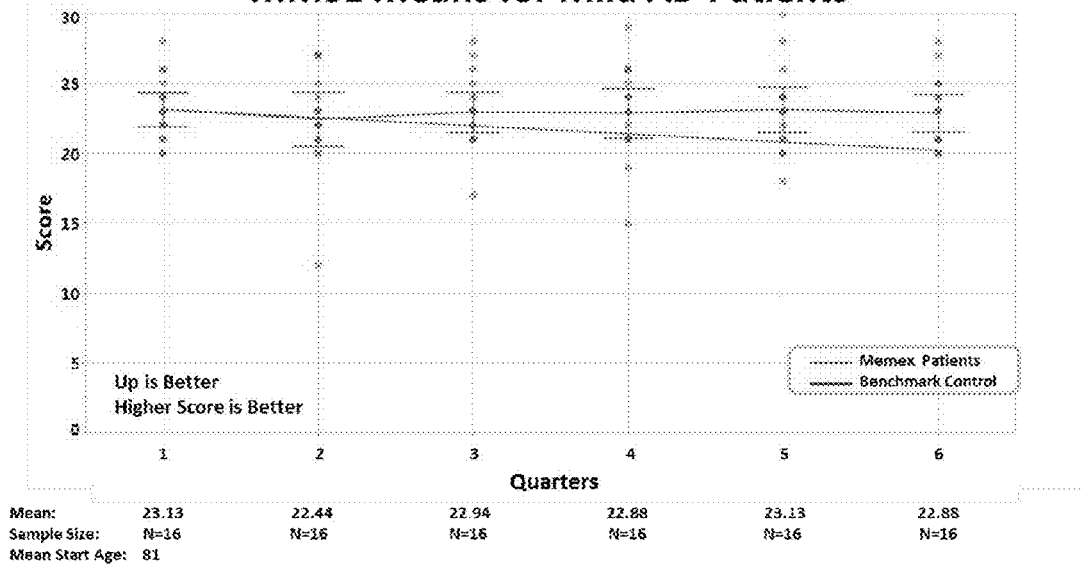
Fig 3: Percent Change in MMSE Scores over 18 Months.
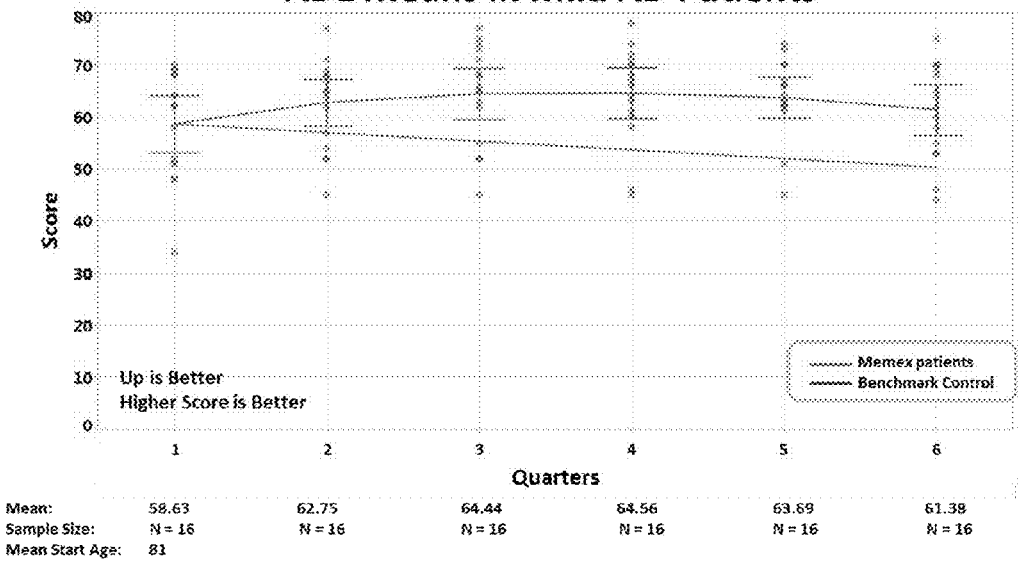
Fig 4: Percent Change in ADL Scores over 18 Months.

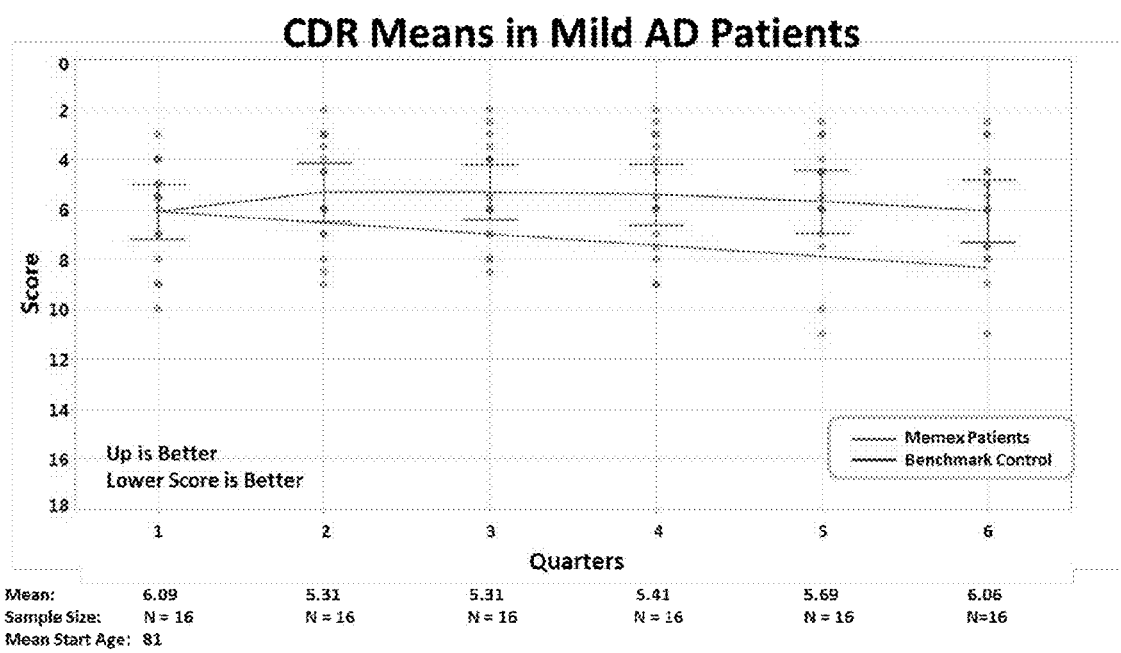
Fig. 5: Percent Change in CDR Scores over 18 Months.

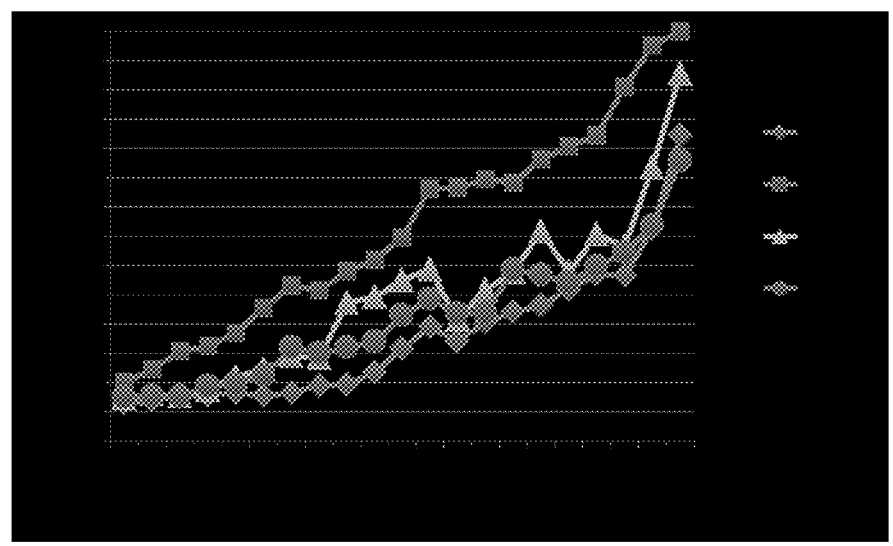
Fig. 6: Memex 100 (green) or Memex 100 Plus (purple) Suppress Faster Fly Neural Aging.

MULTIPATH NUTRITIONAL SUPPLEMENT FOR MEMORY, COGNITION, AND COORDINATION

FIELD OF THE INVENTION

The present invention relates to genetically targeted nutritional supplements of multiple-pathway medicinal extracts designed to treat age-related decline in memory, cognition, and coordination in animals and humans, as may occur in normal aging or in neurological diseases such as Alzheimer's, vascular dementia, amyotrophic lateral sclerosis, Huntington's disease, and Parkinson's diseases. To identify the synergistic nutritional components, genetic targets were identified using genetic methods in *Drosophila* and machine learning techniques on human genetic data bases. Nutritional extracts were then found that act on the identified neural gene targets and tested in *Drosophila* having transgenic beta-amyloid, tau, or Park genes that induce rapid age-related loss of memory, cognition, and/or coordination. The best single and combinations of these nutritional supplements were screened in said transgenic *Drosophila* to identify synergistic combinations of supplements. The optimized multipath supplements have utility as a treatment for age-related chronic disorders such as deteriorating memory, poor cognition, and declining muscular coordination. The nutritional supplements also provide potential treatments for neurological diseases such as Alzheimer's and other forms of neural disease as evidenced by a double-blind, placebo-controlled clinical study of a subset of the components described herein.

BACKGROUND OF THE INVENTION AND DESCRIPTION OF THE PRIOR ART

In the last 20 years, there has been an explosion of knowledge about the science of aging and age-related disease. All life forms on earth have evolved through natural selection, which selects the best genotype for fitness in a particular ecological niche. In 1952 the British Nobel zoologist Peter Medawar proposed that aging is the simple result of the failure of natural selection to maintain fitness in older animals with declining fertility. As fertility wanes, then the chances to correct inappropriate gene expression via natural selection also decline, generating the aging phenotype. Thus, according to Medawar's hypothesis, aging is indirectly caused by the declining forces of natural selection to select the best fitness genes for the aged animal as reproduction capacity declines. In 1957, George Williams further developed Medawar's evolutionary theory of aging by introducing the concept of antagonistic pleiotropy, wherein a gene may promote fitness in young fertile animals (and thus be selected for) but become a liability late in life leading to a subsequent decline in fitness. Modern versions of Medawar's and William's evolutionary theories of aging are still widely believed today by most experts in aging science, as the theory fits well with the immense body of literature showing that natural selection is responsible for virtually all of the phenotypes present in the diverse species observed in Nature. Evolution appears to evolve a life history for each species that is best adapted to its ecological niche.

Besides its sound theoretical basis in the well-known mechanisms of natural selection, the Evolution Theory of Aging has also been directly tested in *Drosophila melanogaster* by Michael Rose at UCI. If the Evolution Theory of Aging was correct, Dr. Rose predicted that he should be able to select populations of long lived animals by simply selecting for reproductive longevity. To carry out his longevity experiment, Dr. Rose started with 5 lines of wild type *Drosophila* flies and selected for reproductive longevity over a 27 year period. Within a few years, Dr. Rose could tell that he was successfully generating longer lived flies by selecting each generation for late fertility. He finally obtained robust Methuselah flies with a demonstrated lifespan of some 3 to 4 times that found in the non-selected control lines, while retaining fertility and sexual vitality.

Several independent experiments have confirmed that these Methuselah flies are indeed long lived compared to wild type flies. These studies show that the selected Methuselah O and SO flies have about a 300% longer mean lifespan than the non-selected wild type B flies. This selection experiment is a dramatic verification that evolution has dominating effects on the aging process.

Current genetic work on Methuselah flies has shown that several hundred genes have an altered expression when selecting for longevity. These experimental results are fully consistent with the Evolution Theory of Aging, which predicts that aging leads to poorly functioning organisms as natural selection to correct optimal gene function wanes with age. Research suggests that the alterations in the expression of scores of genes during aging require a multi-pronged treatment strategy to address the large number of changes in gene expression. Since aging is closely linked with age-related diseases, the hundreds of gene expression changes with age put into question the dominant paradigm of the pharmaceutical industry to develop drug treatments for particular age-related disease using a single compound to target a single biochemical pathway.

Because so many of the identified age-related longevity genes are linked to neural function, there exists a need for multi-gene targeted treatments for memory loss, cognition, neural function, and neural disease. The present combination of herbal extracts and highly purified components of plants target as many of the complementary age-related, neural genetic pathways as possible and act on genetic pathways that were discovered by analyzing genetic changes in long lived fly populations and using machine learning to analyze human gene banks on aging populations. Potential treatments for various neural dysfunctions were identified using existing screening assays for beta-amyloid, tau, and Park *Drosophila* models of Alzheimer's disease or Parkinson's disease.

SUMMARY OF THE INVENTION

Among various aspects of the inventions is a synergistic composition of medicinal herbal extracts for enhancing mental and neuronal functions. The composition may consist of and alternatively may comprise individually or in various synergistic combinations 4 medicinal herbal components. In some embodiments the composition may comprise the herbal extracts of *Astragalus* extract, *Gastrodia elata*, *Vaccinium uliginosum*, and L-Theanine, such as in combination 4.

In other embodiments, the composition also includes extracts of *Schisandra chinensis* berry, Genistein, Lithium, and Selenium such as in combination 8. In other various embodiments Berberine, piperine, Methyl Folate, and Methyl B-12 are added to improve efficacy of genetic modulation of specific genetic targets, such as in combination 12. In other such embodiments Astragaloside IV was added to enhance the potency of the *Astragalus* extract, such as in combination 13. The compositions of combinations 4, 8, 12, and 13 are synergistic nutritional supplements that have high potential for enhancing mental and neural function. In particular, said compositions should have utility in enhancing mental and neural functions in advanced age or in neurological diseases such as Alzheimer's and other forms of neural dysfunction. Said compositions are potent multipath nutritional supplements for optimizing neural function in mammals with a high safety profile.

BRIEF DESCRIPTION OF THE DRAWINGS

FIGS. 1A and 1B show typical screens of transgenic Drosophila melanogaster with an inducible tau (FIG. 1A) or Abeta (FIG. 1B), which greatly reduces neural function with age. To assay for fly behavior changes as neural dysfunction progresses, timed crawl tests in which the time it takes individual flies to climb to the top of a test vial were performed twice each week as the flies aged. Select compositions were screened for use on the transgenic flies using the genetically targeted substances believed to act on longevity genes. Different dose concentrations were tested. Two hundred flies (1 fly of each sex in each of 100 vials) for each test condition were used. RU-486 was added to all fly samples except the untreated controls named Untreated (dashed blue line) and the A+P+T Control) about 4-5 days after flies were placed in vials. The first crawl tests were started about 9-10 days after insertion into vials and 5-6 days after RU addition (see FIGS. 1A and 1B). In Untreated Controls (dashed blue line), young flies typically crawl to the top of the vial quickly in 7-10 seconds, while older flies have progressively longer crawl times of up to 40 seconds or more with advancing age. The RU Controls (solid blue line) were treated with RU-486 without any helper substance and therefore have poor crawling tests and die early at 7 weeks (tau in FIG. 1A) or 5 weeks (Abeta in FIG. 1B). The RU Controls also have elevated crawl times in the very first crawl test because the RU was added some 5-6 days earlier than the first crawl test, which permits deleterious effects to occur early on in RU Controls. FIGS. 1A and 1B show that all of the genetically targeted compositions act to reduce crawl times at all ages of the RU-treated transgenic flies. The single substances and substance combinations are shown by the one letter codes: A=*Astragalus*, P=*Pterocarpus*, T=L-Theanine, G=Genistein, B=Berberine, L=Lithium, and S=Selenium. Note that *Vaccinium uliginosum* was substituted for *Pterocarpus* and *Schisandra chinensis* was substituted for Berberine, because these tested better or had a better safety profile. Mementin in FIG. 1A (dashed purple line) is a FDA approved drug for Alzheimer's Disease and it works very well in our AD tau flies.

FIG. 2 shows transgenic Drosophila melanogaster with an inducible tau. The Untreated Control (dashed blue line) and RU-Control (solid blue line) flies are as described in FIG. 1. The optimal drug combination is the Base 7 Combo A+P+T+G+B+L+S (solid orange line) where the added substances are given by the one letter codes: A=*Astragalus*, P=*Pterocarpus*, T=L-Theanine, G=Genistein, B=Berberine, L=Lithium, and S=Selenium. Note that *Vaccinium uliginosum* was substituted for *Pterocarpus* and *Schisandra chinensis* was substituted for Berberine, because these tested better or had a better safety profile while acting on similar genetic pathways.

FIG. 3 shows a graphical representation of data related to a double-blind, placebo-controlled clinical trial using Base 8 Combo known as Memex 100. FIG. 3 illustrates mean scores (green lines) of MMSE. Only 16 patients took active Memex treatment for the full 18 months. In place of the small number of placebo patients, the mean MMSE scores for the large number of mild patients in the published Benchmark Study results (red line) were plotted as the de facto placebos. The large number of patients in the placebo-like Benchmark Study gave nearly identical declines when compared to the final decline measured in the 4 actual placebo patients that completed the clinical. The scores for the Memex 100 treated individual patients are shown as green dots.

FIG. 4 shows ADL clinical data on Mild AD Patients treated with Memex 100. The mean ADL scores were plotted for 16 mild AD patients treated with Memex 100, who had scored over 20 in their initial MMSE test. The mean ADL clinical scores for the Memex-treated mild AD patients are shown in green along with like data from the published Benchmark Study results (red line) as the de facto placebos. The ADLs for the individual Memex treated moderate AD patients are shown as green dots for each testing time.

FIG. 5 shows CDR clinical data on Mild AD patients treated with Memex 100. For the mild AD patients treated with Memex 100, the mean CDR clinical scores for the Memex-treated mild AD patients are shown in green along with like data from the published Benchmark Study results (red line) as the de facto placebos. The CDR scores for the individual Memex treated moderate AD patients are shown as green dots for each testing time. For the mild AD patients treated with Memex 100, the mean CDR clinical scores for the Memex-treated mild AD patients are shown in green along with like data from the published Benchmark Study results (red line) as the de facto placebos. The CDR scores for the individual Memex treated moderate AD patients are shown as green dots for each testing time.

FIG. 6 shows that Memex 100 (Base 8) and Memex 100+ (Base 12). Suppress Effects of Parkinson's Disease (PD) gene. The Y axis shows average crawl times in seconds for reaching the top of the vial and the X axis shows age in time unit intervals of about 3.5 days. In the Control flies (blue diamonds), the flies do not express the PD gene and naturally crawl slower as they get older. In the flies expressing the PD gene the untreated flies (RU as red squares) crawl slower at every age. Importantly, the flies expressing the PD gene treated with Memex 100 (green triangles) or Memex 100+ (purple circles) are largely protected from the negative effects of the PD gene.

DETAILED DESCRIPTION OF THE INVENTION

Earlier genetic work on wild type and Methuselah flies has shown that several hundred genes have an altered expression pattern when selecting for longevity. Genetic sequencing of the wild type and Methuselah flies has confirmed that several hundred genes appear to be altered in the long lived flies. These experimental results are fully consistent with the Evolution Theory of Aging, which predicts that aging leads to poorly functioning organisms as natural selection for optimal gene function wanes with age. This research suggests that alterations in the expression of scores of genes during aging require a multipath treatment strategy to address the large number of changes in gene expression with age. Since aging is closely linked with the age-related diseases, the hundreds of gene expression changes with age challenge the dominant paradigm of the pharmaceutical industry that the best way to develop effective drug treatments for particular age-related diseases is to develop a single compound to target a single biochemical pathway. Combinations of herbal extracts that target as many of the complementary age-related pathways as possible that act on neurodegeneration with age have thus been identified. Herbal extracts and purified botanicals that act on our identified age-related genes were screened.

. An animal screen known to produce accelerated losses of memory, cognition, and coordination was necessary to screen substances for optimal neronal function as a function of ager. Thus, three *Drosophila* fly lines that have inducible expression of the human Alzheimer's Abeta, tau, or Park gene were developed. When the Abeta or tau gene is activated with the inducing drug RU-486, the fly's neurons become more dysfunctional as they age. To assay for fly neural functional decline with age as Abeta, tau, or the Park gene is induced, crawl times were used to test substances initially picked from the genomics work. It was found that all of the genetically targeted substances act on neural genes and reduce crawl times at each age. FIG. 1 shows examples of this screening data for both the Abeta (FIG. 1A) and tau (FIG. 1B) transgenic fly lines.

Empirical transgenic fly screening data was used to select substances that act with synergistic effectiveness on particular neural gene targets. While there are many claims that a particular substance or herbal extract is "anti-aging" or is a treatment for Alzheimer's or dementia we found that these claims were typically based on insufficient evidence and acted on only on one or two pathways essential to the functional decline in aging and neural disease. The present approach to treating neural functional decline using synergistic compositions is novel in several ways. First, neuronal genetic targets using *Drosophila* longevity genes (as described above) and machine learning technologies using both the *Drosophila* genes and human genes involved in late onset Alzheimer's disease (AD) or Parkinson's disease (PD) were developed. Second, known human Alzheimer's or Parkinson's genes in inducible stocks of transgenic *Drosophila* were used to generate neuronal dysfunction in the flies. This transgenic system provided a viable screen for single and combination substances that were effecting in enhancing neural function. Identification of age-related neural targets and rapid *Drosophila* screens were both essential to producing efficacious synergistic compositions. Finding an effective multipath combination treatment for age-related disease would be an enormous challenge, if not impossible, without using strategies like these. Substances that act as a synergistic treatment for neural dysfunction are described below.

*Astragalus membranaceus* root is a component in some embodiments. It is believed that *Astragalus membranaceus* root (often in concert with other herbs) strengthens immune function during viral (e.g. chronic hepatitis) or bacterial infection or in those individuals undergoing dialysis for kidney failure and also helps in wound healing.

*Astragalus* was tested because it contains several compounds that are active on genes believed to promote longevity and neural function. For example, mTOR (mammalian Target of Rapamycin) is inhibited by *astragalus* extracts. The mTOR protein is involved in cell autophagy (the cellular waste system) and mTOR inhibition promotes autophagy and extends lifespan in mice and flies. As long lived non-dividing cells, neurons are dependent on healthy levels of cell autophagy. *Astragalus* inhibits Microtubule Star (PP2A), a protein phosphatase that alters tau phosphorylation levels, which affects the levels of tau tangles linked to Alzheimer's diseases and dementia. Microtubule Star was strongly linked to longevity and neuronal function in the genetic and machine learning screens. *Astragalus* extracts may also inhibit beta-amyloid production, which is another pathway linked to Alzheimer's disease. The preferred *Astragalus* extracts for the current invention are 3:1 to 5:1 extracts given at a dose of 5 to 15 mg per Kg of body weight.

In other embodiments the composition may also include *Gastrodia elata* tuber. Extracts of *Gastrodia elata* are inhibitors of the neurotransmitter acetylcholinesterase, which was identified in genetic screening and is well known drug target in Alzheimer's disease. *Gastrodia elata* is believed to be effective in treating nervous system disorders and is known to increase vascular circulation and GABA levels in the brain. *Gastrodia elata* also reduces brain inflammation, which studies indicate is critical to optimizing brain cell function and regeneration. The preferred extracts for the current invention are extracts of *Gastrodia elata* tuber standardized to 10% to 30% (weight/weight) of Gastrodin, and given at a dose of 3 to 10 mg *Gastrodia elata* extract per Kg of body weight.

In other embodiments the composition may also include *Vaccinium uliginosum* (a Eurasia bog bilberry) because of its positive effects on increasing the insulin sensitivity pathway and reducing the inflammatory factors TNF-alpha and the prostaglandin PGE2. These pathways are important for longevity and neuronal functioni. *Vaccinium uliginosus* is found in cool mountain regions of Europe, Mongolia, northern China, Sierra mountains in California, and the Rocky Mountains in North America. In some embodiments, the extracts are derived from *Vaccinium uliginosum* berries that are highly enriched for their flavonoids (the active ingredients). The preferred *Vaccinium* extracts are standardized for 20% (weight/weight) Pterostilbene and given at a dose of 0.5 to 2.5 mg per Kg of body weight.

In other embodiments the composition may also include L-theanine, which alters the expression of Excitatory Amino Acid Transporters (EAATs), which are longevity and neuronal target genes identified through genetic and machine-learning screens. EAATs are trans-membrane proteins involved in the neuronal uptake of glutamate in the glutamatergic neurotransmitter signaling. The L-theanine (also known as gamma-glutamylethylamide, or 5-N-ethyl-glutamine) is an uncommon amino acid found preferentially in green tea. Theanine is an analog of glutamine and glutamate and can cross the blood-brain barrier, so it has direct effects on the brain. Among its psychoactive properties, theanine is reported to reduce metal stress and improved cognition and mood via its expected binding to the GABA brain receptors in the parasympathetic nervous. Thus theanine appears to increase the overall level of the brain inhibitory transmitter GABA and is reported to promote alpha wave production in the brain.

L-Theanine also increases brain dopamine concentrations and has significant affinities for the AMPA, Kainate, and NMDA receptors. The AMPA receptor is a non-NMDA trans-membrane receptor for glutamate that mediates fast synaptic transmission in the central nervous system. Kainate receptors are non-NMDA receptors that respond to the neurotransmitter glutamate, which have been implicated in inhibitory neurotransmission via promoting the release of the inhibitory neurotransmitter GABA. The NMDA receptor is a glutamate receptor and helps control memory and synaptic plasticity. L-Theanine may also have positive effects on serotonin levels. In rats, L-Theanine has been shown to be neuroprotective. All of these psychoactive properties of L-Theanine make it an excellent component of a multipath nutritional supplement for promoting memory and cognition.

Extracts of *Astragalus membranaceus, Gastrodia elata* tuber extract, and *Vaccinium uliginosum*, and L-Theanine (A+G+V+T) make up the Base 4 Combo combination that enhances mental and neuronal function in a *Drosophila*. In a favored embodiment of the invention, the said Base 4 composition is taken by humans at a dose of 5 to 15 mg per Kg of body weight per day to provide nutritional support in the form of a dietary supplement.

The Base 4 Combo composition comprises 3:1 to 5:1 extracts of said *Astragalus membranaceus, gastodia elata* standardized for 10% to 20% (weight/weight) gastrodin, greater than 5:1 extracts of said *Vaccinium uliginosum* berries, and more than 95% (weight/weight) purity of L-Theanine from natural or synthetic sources.

In the Base 4 Combo, the dosage of said *Astragalus membranaceus* extract is 5 to 15 mg per Kg of body weight per day, the dosage of *gastrodia elata* is 3 to 10 mg per Kg of body weight per day, the dosage of said *Vaccinium uliginosum* berry extract is 0.5 to 2.5 mg per Kg of body weight per day, and the dosage of L-Theanine is 0.6 to 2.3 mg per Kg of body weight per day.

One early example of our screening methods is shown in FIG. 1A using the Alzheimer's Disease (AD) transgenic fly assay. In FIG. 1A the RU Control (solid blue line) induces human tau production (cause tangles in AD patients) in the *Drosophila* brain and this induces rapid age-dependent loss of crawling ability (Note that there are two crawl tests per week). In the Untreated Controls with no tau expression (dashed blue line), the flies are fast crawlers and only gradually lose crawling speed as they grow older. FIG. 1A demonstrates that the 3-component (A+P+T shown as red line) core composition performs about as well in delaying neuronal dysfunction as Mementin treated RU flies (dashed purple line), which is a FDA approved treatment for Alzheimer's disease. FIG. 1A also shows that the individual components *Astragalus* (A—solid black line) and *Pterocarpus* (P—dotted line) are not as good as the combination of A+P+T. Note that the *Pterocarpus* extract in this figure was later substituted with *Vaccinium uliginosum* extract, which performed as well (both herbs were standardized for the same active flavonoids) and was more reliable to source. Another single component tested is Pine Bark OPCs (PB—green line), which is an example of a component with low efficacy that was not included in any combination. Finally, FIG. 1A shows that A+P+T can even slow the loss of climbing ability in normal aging flies (A+P+T—red dash-dot line). Taken as a whole, these data indicate that treatment with the critical combination of substances A+P+T can effectively treat neuronal dysfunction with age or disease.

In other embodiments the composition may also include Genistein in addition to the components of the Base 4 composition. Genistein is a phytoestrogen isoflavone that acts on Pre-mRNA Processing Factor (PRP8) and the Estrogen Receptor, which are two very important genes that were strongly linked to longevity and neuronal function in our genetic and machine learning screens. Genistein also acts to down regulate beta-amyloid, glut-1 and presenilin. Genistein is also reported to increase PPAR, autophagy, and Nrf-2 antioxidant response. All of these additional functions promote longevity and neural function. The dosing fly experiments suggest including 0.2 to 0.6 mg per Kg of body weight as a daily dose of more than 95% (weight/weight) pure Genistein from natural or synthetic sources.

Berberine is a natural polyphenolic compound that is found in the Chinese herb *Rhizoma coptidis* and many other medicinal plants. In other embodiments the composition may also include Berberine which comines synergistically with the other components of the Base 4 composition. Berberine contains an inhibitor of tau phosphorylation and also modulates beta amyloid production and the neurotransmitter acetylcholine. These pathways are strongly linked to longevity in the genetic and machine-learning screens and to neuronal function through the current literature. The dose of Berberine 0.8 to 3.0 mg per Kg of body weight as a daily dose of more than 95% (weight/weight) pure Berberine from natural or synthetic sources In other embodiments the composition may also include *Schisandra chinensis* berry extract in addition to the other components of the Base 4 composition. *Schisandra* extracts reduce TNF-alpha, IL-1B, IL-6, Abeta, and cortisol to reduce neural inflammation. *Schisandra* also induces protective Nrf2 and HO-1 transcription and promotes cholinergic signaling. These pathways are strongly linked to longevity in the genetic and machine-learning screens and to neuronal function though the current literature. The dose of *Schisandra chinensis* berry extract should be 2-7 mg per kg of body weight.

In certain other embodiments, the low-dose mineral component Lithium (as Lithium orotate or Glycinate salt) may also be added. Lithium acts on several genetic pathways that Genescient found to be important in longevity and neuronal function. For example, lithium acts on NCS-1/Frequenin, which codes a calcium-binding protein involved in neurotransmitter release. Other important neural pathways affected by lithium include autophagy, tau phosphorylation, and neural transmitter breakdown by acetylcholinesterase. These are very important pathways for neural function. In certain embodiments, adding lithium at an optimallyvery low dose, has been shown to repair neural function. Experiments suggest a human lithium dose of about 15 to 72 microgram per Kg of body weight per day, which is typically provided as a Lithium Orotate salt, but Lithium Glycinate or Lithium Carbonate can also be used.

In other embodiments a low-dose mineral component Selenium (normally as a selenium amino acid complex) can be added. Selenium was chosen for fly screening because it acts on the Pre-mRNA-Processing splicing Factor 8 (PRPF8) and Excision Repair Cross-Complementing 1 (ERCC1) PRP8 plays an essential role in mRNA processing; ERCC1 is important for DNA repair, which is inhibited by neurofibrillary tangles. Selenium also acts as a cofactor in many selenoproteins, which can help prevent beta-amyloid aggregation and aluminum detoxification. It has been shown that selenium can protect against dementia in our AD *Drosophila* transgenics with induced human Abeta or tau expression. Experimental data suggests an optimal human dose of Selenium of about 0.6 to 2.9 micrograms per Kg of body weight per day, which is provided as a Selenium amino acid chelate.

In other embodiments Piperine may also be included in the composition to increase bioavailiablity of the various other components of the composition. Piperine is the active component of black pepper extract, The above 9 combo components are all made more bioavailable by the inclusion of small amounts of piperine or the commercial piperine trademarked product BioPerine®. Besides providing greater bioavailability, piperine is also reported to reduce beta amyloid plaques and tau tangles and improve memory in a rat Alzheimer model. The favored Piperine (>95% weight/weight purity) dose is 0.1 to 0.25 mg per Kg of body weight per day. BioPerine® is a standardized brand of piperine that can be used in the formulation at the same dose as piperine. Note that piperine is an insecticide and thus cannot be tested in the fly experiments. However, because piperine does provide greater bioavailability for mammals, it is included in the final composition.

With the addition of Piperine, a Base 10 Combo composition comprising and alternatively consisting or consisting essentially of *Astragalus* extract, *Gastrodia elata* extract, *Vaccinium uliginosum* extract, L-Theanine, Genistein, Berberine, *Schisandra chinensis* berry extract, Lithium, Selenium, and Piperine is formed. The said 10 component composition is taken by humans at a dose of 10 to 30 mg per Kg of body weight per day as a method to provide nutritional support for memory, cognition, and neuromuscular coordination. The said 10 component composition is also taken by humans at a dose of 10 to 30 mg per Kg of body weight per day as a method to provide nutritional support for humans suffering from mental senility or dementia as may occur in normal aging. The said 10 component composition is also taken by humans at a dose of 10 to 30 mg per Kg of body weight per day as a method to provide nutritional support for humans suffering from neurological diseases such as Alzheimer's disease, vascular dementia, amyotrophic lateral sclerosis, Huntington's disease, and Parkinson's disease.

As another embodiment, the said 10 components generate a unique composition of matter that can be used as dietary supplement in mammals at a dose of 10 to 30 mg per Kg of body weight per day as a method for enhancing neural function in dogs, cats, and horses.

Previous AD *Drosophila* screens have shown that the supplement of 7 components with *Pterocarpus marsupium* in place of *Vaccinium uliginosum* was able to abolish much of the AD effect in tau mutant AD flies. For example, FIG. 2B shows that Base 7 Combo substances (A+B+P+T+G+L+S) are better than 6 component combos missing selenium (A+B+P+T+G+L) or lithium (A+B+P+T+G+S) at suppressing the dementia induced by human tau expression in our AD transgenic flies. The individual substances in the combinations are shown by one letter codes: A=*Astragalus*, B=Berberine, P=*Pterocarpus*, T=L-Theanine, G=Genistein, L=Lithium, and S=Selenium. This is a subset of the Base 10 core Combo that is missing *Gastrodia elata, Schisandra Chinensis*, and Piperine.

More advance genetic and lab work has indicated that 2 other components can be added to the Base 10 Combo of *Astragalus* extract, *Gastrodia elata* extract, *Vaccinium uliginosum* extract, L-Theanine, Genistein, Berberine, *Schisandra chinensis* berry extract, Lithium, Selenium, and Piperine. The 11th and 12th components are the active methylated forms of Folate (5-MTHF) and methyl B-12. It has been estimated that some 40% of Americans have only one active gene for converting Folate to the active methyl folate form and 10% of Americans lack both active genes. The active forms of these vitamins are typically not present in food and many people are deficient in methyl Folate or methyl B-12, leading to neurological dysfunction. The favored human dose is about 600 mcg per day Methyl Folate (5-MTHF) and about 500 mcg per day Methyl B-12.

With the addition of Methyl Folate and Methyl B-12, we get a Base 12 Combo of *Astragalus* extract, *Gastrodia elata* extract, *Vaccinium uliginosum* extract, L-Theanine, Genistein, Berberine, *Schisandra chinensis* berry extract, Lithium, Selenium, Piperine, Methyl Folate, and Methyl B-12. The said 12 component composition is taken by humans at a dose of 10 to 30 mg per Kg of body weight per day as a method to provide nutritional support for memory, cognition, and neuromuscular coordination. The said 12 component composition is also taken by humans at a dose of 10 to 30 mg per Kg of body weight per day as a method to provide nutritional support for humans suffering from mental senility or dementia as may occur in normal aging. The said 12 component composition is also taken by humans at a dose of 10 to 30 mg per Kg of body weight per day as a method to provide nutritional support for humans suffering from neurological diseases such as Alzheimer's disease, vascular dementia, amyotrophic lateral sclerosis, Huntington's disease, and Parkinson's disease.

As another potential embodiment, Astragaloside IV (the major active component of *Astragalus*) is added to the Core 12 mix to create the Core 13 mix. Astragaloside IV comes from the whole root of *Astragalus membranaceus* and has human dose of 5 to 10 mg per day. The preferred Astragaloside IV is greater than 70% (weight/weight) pure. The Astragaloside IV component is synergistic with the wide spectrum 3:1 to 5:1 extract of *Astragalus membranaceus*.

The present invention discloses compositions and treatments for neural conditions that use the Base 4, Base 10, Base 12, or Base 13 herbal combinations. Without the present screening strategy of genetic and machine learning, it would not have been possible to identify the complementary neural function targets. And without the transgenic Alzheimer and Parkinson flies, it would not have been possible to screen various combinations and doses to test for synergistic effectiveness. There is no record in the published literature that the particular Base 4, Base 10, Base 12 or Base 13 substance combinations were ever used in herbal compositions over the thousands of years of herbal practice despite the favored use of *Astragalus membranaceus* in Chinese medicine. The components of the Base 4, Base 10, Base 12 and Base 13 supplements act on a critical number of genetic pathways to permit a synergistic impact on longevity and neural function.

While the many embodiments of the invention have been disclosed above and include presently preferred embodiments, many other embodiments and variations are possible within the scope of the present invention. Accordingly, the details of the preferred embodiments and examples provided are not to be construed as limiting. It is to be understood that the terms used herein are merely descriptive rather than limiting and that various changes, numerous equivalents may be made without departing from the spirit or scope of the claimed invention.

For oral administration as a capsule, suitable binders, controlled-release agents, lubricants, disintegrating agents, lecithin, and coloring agents can also be incorporated into the mixture. Suitable binders and controlled-release agents include starch, gelatin, natural sugars such as glucose or beta-lactose, corn sweeteners, natural and synthetic gums such as acacia, guar, konjack, or sodium alginate, carboxylmethylcellulose, hydroxypropyl-methylcellulose, polyethylene glycol, waxes, and the like. Lubricants used in these dosage forms include sodium oleate, sodium stearate, magnesium stearate, micro-crystalline cellulose, sodium benzoate, sodium acetate, sodium chloride, silica, and the like. Disintegrators include, without limitation, starch, methylcellulose, agar, bentonite, xanthan gum, and the like. Other biologically inactive components which can be incorporated into the compositions of the present invention include colorings, calcium carbonate, calcium citrate, magnesium citrate, magnesium oxide, magnesium hydroxide, flavorings, preservatives, flow-enhancers, filling aids, essences, and other aesthetically pleasing components. As a powder for use in water or other liquid, sweeteners can be added, which include plant-based sugars such as sugar, high fructose corn syrup, and stevia extract, as well as artificial sweeteners such as sucralose, acesulfame potassium, and aspartame.

Examples of suitable forms for dried extract administration as a capsule supplement can include tablets, capsules, and soft gels. The tablet, capsule, or softgel can be coated with a substance capable of protecting the capsule composition from disintegration in the esophagus but will allow disintegration of the composition in the stomach and mixing with food to pass into the patient's small intestine. The polymer can be administered alone or in combination with a nutraceutical acceptable carrier, diluent or excipient substance, such as a solid, liquid or semi-solid material. Examples of suitable carriers, diluents and excipients include lecithin, vegetable oil, lactose, dextrose, sucrose, sorbitol, mannitol, starches, gum acacia, alginates, tragacanth, gelatin, calcium silicate, cellulose e.g., magnesium carbonate or a phospholipid with which the polymer can form a micelle.

Clinical Trial shows cognitive stability for most patients treated for mild Alzheimer's disease. The composition of the Base 8 Combo (aka Memex 100) was used in a random double-blind, placebo-controlled Clinical Trial of Alzheimer's Disease patients, where subjects took two serving of a 480 mg capsule per day or two serving of similar placebo capsule per day for up to 18 month to see potential positive or negative changes on cognition tests and Activities of Daily Living. Memex 100 has (A+P+T+G+B+L+S+Pi), where A=*Astragalus*, P=*Pterocarpus*, T=L-Theanine, G=Genistein, B=Berberine, L=Lithium, and S=Selenium and Pi=Piperine. Note that in the current application, *Vaccinium uliginosum* has been substituted for *Pterocarpus*, and *Gastrodia elata, Schisandra chinensis*, Methyl Folate, Methyl B12, and Astragaloside IV have been added because these showed improved results while acting on the same genetic pathways.

In the trial over 40 Alzheimer's patients were treated with Memex 100 or placebo for up to 18 months. Both test and placebo patients continued their prior drug and lifestyle during and after the trial. Each patient was tracked at 3 month intervals in the trial using three standard AD surveys: Mini-Mental Status (MMSE), Activities of Daily Living (ADL), and Clinical Dementia Rating (CDR). MMSE, ADL, and CDR were tested before starting the trial and every 3 months after starting for up to 18 months duration. To maximize the number of AD patients that would take the active botanical drug, over 35 patients were given Memex 100 and only 5 patients were placed on placebo. To make up for the small number of placebo patients (only 4 completed the trial), the data on our treated patients was compared to published data from 471 AD patients of matched demographic and AD symptoms [47] that were treated and tested in a similar manner to the treatment of placebo patients that did not receive Memex 100. The 4 placebo patients closely tracked the loss of cognitive function as measured by MMSE, ADL, and CDR in the 471 segregate placebo patients, but without the large fluctuations that are characteristic of such small patients groups. Moreover, with the large 471 patient clinical study [47] of benchmark placebos, all the Memex treated patients with large numbers of age and condition matched surrogate placebo controls.

Memex 100 stabilized MMSE clinical test scores in the AD patients. While many AD patients discontinued treatment early (the clinical trial was initially set for only for 12 months), most continued Memex 100 treatment for 18 months and MMSE data on these mild patients are shown in FIG. 3 along with the data from comparable patients from the benchmark study of Bernick el al. [47]. The MMSE clinical data on Mild AD Patients in FIG. 3 present a clear trend of stabilizing patient MMSE testing levels.

Memex 100 treatment also stabilized ADL clinical test scores in AD patients. The patients were also scored for Activities of Daily Living (ADL), which is a survey of the functional activities and capabilities of the AD patients on a daily basis. The ADL mean scores are plotted for the mild AD patients in FIG. 4. As before, the ADL scores were also compared to matching data from the published Benchmark study (red line) as our de facto placebo control. The mild AD patients that were treated with Memex 100 (green line) indicated a stabilization of ADL scores in the 18 months of treatment.

Memex 100 treatment also stabilized CDR clinical test scores in the AD patients. The patients were also scored for Clinical Dementia Rating (CDR), which is a numerical scale used to quantify the severity of the dementia symptoms. With the CDR protocol, the patient is assessed on their cognitive and functional performance in six areas with each area having a 0 to 3 ranking where a 0 score has no symptoms and a score of 3 implies severe dementia in that area. The maximum CDR score of 18 means that the patient has the most extreme case of dementia. The CDR mean scores are plotted for the mild AD patients in FIG. 5. As before, the CDR scores (green lines) were also compared to matching data from the published Benchmark study (red line) as our de facto placebo control. As is seen in the other AD metrics, mild AD patients that were treated with Memex 100 (green line) indicated a stabilization of CDR scores in the 18 months of treatment.

FIG. 6 shows a fly experiment with the human transgenic Park gene that develop memory and coordination problems as do the Alzheimer's flies. Here the Base 8 Combo (A+B+P+T+G+L+S+Pi) (Memex 100) as used in the clinical trial was compared with the new Memex 100+, which is the Base 12 Combo described in the present application. Both Memex 100 and Memex 100+ suppress the effects of Parkinson's Disease (PD) gene (FIG. 6). The Y axis shows average crawl times in seconds for reaching the top of the vial and the X axis shows age in time unit intervals of about 3.5 days. In the Control flies (blue diamonds), the flies do not express the PD gene and naturally crawl slower as they get older. In the flies expressing the PD gene the untreated flies (RU as red squares) crawl slower at every age. Importantly, the flies expressing the PD gene treated with Memex (green triangles) or Memex Plus (purple circles) are largely protected from the negative effects of the PD gene. These results show that both treatments are effective with a slight trend toward more effectiveness in Memex 100+. A similar improvement has also been observed with Memex 100+ over Memex 100 with respect to AD flies (result not shown).

The disclosure describes a medicinal herbal composition for enhancing mental and neural functions in normal aging populations and for treating neural disease, comprising a mixture of extracts of *Astragalus membranaceus* roots, *Gastrodia elata* tuber, *Vaccinium* uliginos6 um berries, and L-Theanine. The disclosure also describes a composition comprising 3:1 to 5:1 extracts of said *Astragalus membranaceus* roots and *gastodia elata* tuber, the *gastrodia elata* tuber standardized for 10% to 20% (weight/weight) gastrodin. The composition also comprises greater than 5:1 extracts of said *Vaccinium uliginosum* berries, and more than 95% (weight/weight) purity of L-Theanine from natural or synthetic sources.

Further the disclosure describes a method for enhancing mental and neural functions in normal aging populations and for treating neural disease comprising the steps of providing a dosage of *Astragalus membranaceus* extract at 5 to 15 mg per day per Kg of body weight of a patient, a dosage of *gastrodia elata* at 3 to 10 mg per day per Kg of body weight of the patient, a dosage of said *Vaccinium uliginosum* berry extract at 0.5 to 2.5 mg per day per Kg of body weight of the patient, and a dosage of L-Theanine at 0.6 to 2.3 mg per day per Kg of body weight of the patient.

Additionally the disclosure describes a method for enhancing mental and neural functions in normal aging populations and for treating neural disease comprising the steps of providing a dosage of *Astragalus membranaceus* extract at 5 to 15 mg per day per Kg of body weight of a patient, a dosage of *gastrodia elata* at 3 to 10 mg per day per Kg of body weight of the patient, a dosage of said *Vaccinium uliginosum* berry extract at 0.5 to 2.5 mg per day per Kg of body weight of the patient, a dosage of L-Theanine at 0.6 to 2.3 mg per day per Kg of body weight of the patient, and a dosage of 95% (weight/weight) pure Genistein from natural or synthetic sources at 0.2 to 0.6 mg per day per Kg of body weight of the patient.

The invention claimed is:

1. A tablet or capsule for treating Alzheimer's disease, dementia or Parkinson's disease in a human, the table or capsule consisting essentially of therapeutically effective amounts of:
   *astragalus membranaceus* roots,
   *gastrodia elata* tuber,
   *vaccinium uliginosum* berries, and
   L-theanine.

2. The tablet or capsule of claim 1, wherein
   the therapeutically effective amount of *astragalus membranaceus* roots is approximately 5 to 15 mg;
   the therapeutically effective amount of *gastrodia elata* tuber is approximately 3 to 10 mg;
   the therapeutically effective amount of *vaccinium uliginosum* berries is approximately 0.5 to 2.5 mg; and
   the therapeutically effective amount of L-theanine is approximately 0.6 to 2.3 mg.

3. The tablet or capsule of claim 1, further consisting essentially of therapeutically effective amounts of: genistein.

4. The tablet or capsule of claim 3, wherein
   the therapeutically effective amount of genistein is approximately 0.2 to 0.6 mg.

5. The tablet or capsule of claim 3 further consisting essentially of therapeutically effective amounts of:
   berberine.

6. The tablet or capsule of claim 5, wherein
   the therapeutically effective amount of berberine is approximately 0.8 to 3.0 mg.

7. The tablet or capsule of claim 5 further consisting essentially of therapeutically effective amounts of:
   *schisandra chinesis* berry extract.

8. The tablet or capsule of claim 7, wherein
   the therapeutically effective amount of *schisandra chinesis* berry extract is approximately 2 to 7 mg.

9. The tablet or capsule of claim 7 further consisting essentially of therapeutically effective amounts of:
   a lithium salt.

10. The tablet or capsule of claim 9, wherein
    the therapeutically effective amount of lithium salt is approximately 15 to 72 mcg.

11. The tablet or capsule of claim 9, wherein
    the lithium salt is selected from the group consisting of lithium orotate, lithium carbonate, and lithium aspartate.

12. The tablet or capsule of claim 9 further consisting essentially of therapeutically effective amounts of:
    selenium amino acid chelate.

13. The tablet or capsule of claim 12, wherein
    the therapeutically effective amount of selenium amino acid chelate is approximately 0.6 to 2.9 mcg.

14. The tablet or capsule of claim 12 further consisting essentially of therapeutically effective amounts of:
    piperine.

15. The tablet or capsule of claim 14, wherein
    the therapeutically effective amount of piperine is approximately 0.1 to 0.25 mg.

16. The tablet or capsule of claim 14 further consisting essentially of therapeutically effective amounts of:
    methyl folate; and
    methyl B-12.

17. The tablet or capsule of claim 16, wherein
    the therapeutically effective amount of methyl folate is approximately 600 mcg; and
    the therapeutically effective amount of methyl B-12 is approximately 500 mcg.

18. The tablet or capsule of claim 16 further consisting essentially of therapeutically effective amounts of:
    astragaloside IV.

19. The tablet or capsule of claim 18, wherein
    the therapeutically effective amount of astragaloside IV is approximately 5 to 10 mg.

* * * * *